United States Patent
Lee et al.

(10) Patent No.: US 11,407,706 B2
(45) Date of Patent: Aug. 9, 2022

(54) METHOD FOR MANUFACTURING TEREPHTHALATE-BASED COMPOSITION COMPRISING APPLYING PRESSURE

(71) Applicant: LG CHEM, LTD., Seoul (KR)

(72) Inventors: Seok Goo Lee, Daejeon (KR); Sung Kyu Lee, Daejeon (KR); Joon Ho Shin, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 17/273,279

(22) PCT Filed: Sep. 18, 2019

(86) PCT No.: PCT/KR2019/012079
§ 371 (c)(1),
(2) Date: Mar. 3, 2021

(87) PCT Pub. No.: WO2020/111475
PCT Pub. Date: Jun. 4, 2020

(65) Prior Publication Data
US 2021/0317063 A1    Oct. 14, 2021

(30) Foreign Application Priority Data
Nov. 28, 2018    (KR) .................... 10-2018-0149455

(51) Int. Cl.
*C07C 67/03* (2006.01)
*C07C 67/02* (2006.01)
(Continued)

(52) U.S. Cl.
CPC ........... *C07C 67/03* (2013.01); *B01J 19/0006* (2013.01); *C07C 67/02* (2013.01); *C07C 67/48* (2013.01);
(Continued)

(58) Field of Classification Search
CPC .......... C07C 67/02; C07C 67/03; C07C 67/48; B01J 2219/00162
See application file for complete search history.

(56) References Cited

U.S. PATENT DOCUMENTS

| 4,929,749 A | 5/1990 | Gupta et al. |
| 5,101,064 A | 3/1992 | Dupont et al. |

(Continued)

FOREIGN PATENT DOCUMENTS

| EP | 3293226 A1 | 3/2018 |
| JP | 2012-092074 | 5/2012 |

(Continued)

OTHER PUBLICATIONS

Janjua et al., "Systemic Uptake of Diethyl Phthalate, Dibutyl Phthalate, and Butyl Paraben Following Whole-Body Topical Application and Reproductive and Thyroid Hormone Levels in Humans," Environ. Sci. Technol. vol. 41, 2007, 5564-5570.
(Continued)

*Primary Examiner* — Yate' K Cutliff
(74) *Attorney, Agent, or Firm* — Dentons US LLP

(57) ABSTRACT

Provided is a method for manufacturing a terephthalate-based composition, the method comprising:
a step (S1) of flowing in a dialkyl terephthalate in which alkyl has 7 to 10 carbon atoms and a primary alcohol with a low boiling point having 4 or 5 carbon atoms into a reactor and performing transesterification of the dialkyl terephthalate and the primary alcohol with a low boiling point; and
a step (S2) of extracting in a reduced pressure an unreacted material and a by-product from the reactor after finishing the transesterification,
wherein the step S1 comprises a pressure-applying step in which the pressure of the reactor is 1.5 to 2.5 bar.

8 Claims, 1 Drawing Sheet

(51) Int. Cl.
*B01J 19/00* (2006.01)
*C07C 67/48* (2006.01)

(52) U.S. Cl.
CPC .............. *B01J 2219/00029* (2013.01); *B01J 2219/00162* (2013.01)

(56) References Cited

U.S. PATENT DOCUMENTS

| | | | | |
|---|---|---|---|---|
| 5,319,128 | A * | 6/1994 | Dupont | C07C 67/03 560/78 |
| 5,854,377 | A | 12/1998 | Braune | |
| 7,214,723 | B2 | 5/2007 | West | |
| 7,741,509 | B2 * | 6/2010 | Cook | C07C 67/08 560/98 |
| 2004/0106746 | A1 | 6/2004 | Wilhelm et al. | |
| 2004/0242712 | A1 | 12/2004 | West | |
| 2007/0179229 | A1 * | 8/2007 | Grass | C07C 29/141 524/287 |
| 2013/0274393 | A1 | 10/2013 | Peters | |
| 2014/0288325 | A1 | 9/2014 | Yang et al. | |
| 2014/0336294 | A1 | 11/2014 | Kim et al. | |
| 2014/0336319 | A1 | 11/2014 | Kim et al. | |
| 2014/0336320 | A1 * | 11/2014 | Lee | C07C 67/03 524/296 |
| 2015/0025186 | A1 | 1/2015 | Kim et al. | |
| 2015/0225538 | A1 | 8/2015 | Kim et al. | |
| 2015/0232411 | A1 | 8/2015 | Storzum et al. | |
| 2016/0159726 | A1 | 6/2016 | Storzum et al. | |
| 2017/0081501 | A1 | 3/2017 | Kim et al. | |
| 2018/0002268 | A1 | 1/2018 | Kim et al. | |
| 2018/0066125 | A1 * | 3/2018 | Kim | C08K 5/0016 |
| 2018/0163018 | A1 * | 6/2018 | Kim | C07C 69/75 |
| 2018/0171103 | A1 * | 6/2018 | Kim | C08K 5/092 |

FOREIGN PATENT DOCUMENTS

| | | |
|---|---|---|
| KR | 10-1998-7003050 | 9/1998 |
| KR | 10-2003-0068182 | 8/2003 |
| KR | 10-2013-0042743 | 4/2013 |
| KR | 10-2014-0115977 | 10/2014 |
| KR | 10-2014-0132697 | 11/2014 |
| KR | 10-1447376 | 12/2014 |
| KR | 10-2015-0002807 | 1/2015 |
| KR | 10-2016-0130363 | 11/2016 |
| KR | 10-2016-0134098 | 11/2016 |

OTHER PUBLICATIONS

Rahman et al., "The plasticizer market: an assessment of traditional plasticizers and research trends to meet new challenges," Prog. Polym. Sci. vol. 29, 2004, 1223-1248.

* cited by examiner

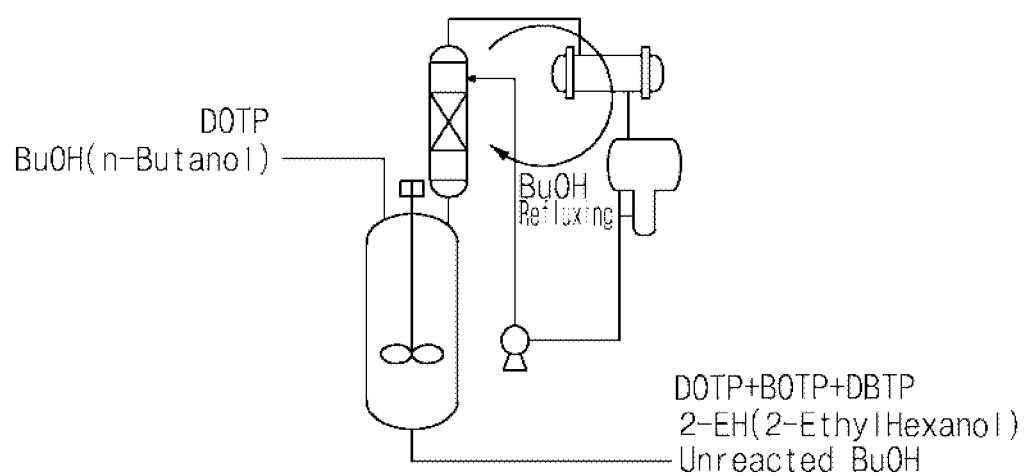

METHOD FOR MANUFACTURING TEREPHTHALATE-BASED COMPOSITION COMPRISING APPLYING PRESSURE

CROSS-REFERENCE TO RELATED APPLICATIONS

This application is a National Stage Application of International Application No. PCT/KR2019/012079 filed on Sep. 18, 2019, which claims the benefit of priority to Korean Patent Application No. 10-2018-0149455, filed on Nov. 28, 2018, the entire disclosure of which is incorporated herein by reference.

TECHNICAL FIELD

The present invention relates to a method for manufacturing a terephthalate-based composition, and particularly, a method for manufacturing a terephthalate-based composition including a pressure-applying step in which the pressure of a reactor in liquid injecting and reacting steps is set to 1.5 to 2.5 bar for preventing the vaporization of a primary alcohol reactant with a low boiling point, thereby accomplishing the reduction of reaction time and the decreasing effects of energy loss.

BACKGROUND ART

Phthalate-based plasticizers account for 92% of the world plasticizer market (see Mustafizur Rahman and Christopher S. Brazel "The plasticizer market: an assessment of traditional plasticizers and research trends to meet new challenges" Progress in Polymer Science 2004, 29, 1223-1248), are additives mainly used for improving processability by imparting polyvinyl alcohol (hereinafter, will be referred to as "PVC") with flexibility, durability, cold tolerance, etc., and decreasing viscosity during melting, are closely connected with practical life more than any material else after being put to PVC in various amounts from hard products such as a rigid pipe to soft products used as a wrapping material for foods, blood storage bags, flooring materials, etc., and are widely used for a usage inducing unavoidable direct contact with the human body.

However, in spite of the compatibility with PVC and excellent impartment with softness of the phthalate-based plasticizer, recently, if a PVC product containing a phthalate-based plasticizer is used in practical life, there are controversy on harmfulness on acting as a suspected endocrine disruptor (environmental hormone) and a carcinogen with the level of heavy metals due to the effusion thereof little by little to the outside (see N. R. Janjua et al. "Systemic Uptake of Diethyl Phthalate, Dibutyl Phthalate, and Butyl Paraben Following Whole-body Topical Application and Reproductive and Thyroid Hormone Levels in Humans" Environmental Science and Technology 2007, 41, 5564-5570). Particularly, after a report has been presented that di-(2-ethylhexyl) phthalate (DEHP) of which amount used is the most among phthalate-based plasticizers is leaked out from a PVC product in the 1960s in the US, and concern on environmental hormone is added in the 1990s, various studies on the harmfulness to the human body of the phthalate-based plasticizers and global environmental regulations thereon have begun.

Accordingly, to cope with the environmental hormone problems and environmental regulations due to the leakage of the phthalate-based plasticizer, many researchers are studying to develop a novel non-phthalate-based alternative plasticizer which excludes anhydrous phthalic acid which is used for preparing a phthalate-based plasticizer, or to develop a technique for suppressing the leakage of the phthalate-based plasticizer for significantly decreasing the risk to the human body and for coinciding the environmental regulations.

Meanwhile, as the non-phthalate-based plasticizer, a terephthalate-based plasticizer is getting the spotlight as a material free from environmental problems as well as having the same degree in view of physical properties as the phthalate-based plasticizer, and various types of terephthalate-based plasticizers are being developed. In addition, research on an equipment for manufacturing such terephthalate-based plasticizer as well as research for developing a terephthalate-based plasticizer having excellent physical properties is being actively conducted, and in view of process design, the design of a more efficient, economic and simple process is required.

A typical terephthalate-based plasticizer can include dibutyl terephthalate, and the dibutyl terephthalate is generally prepared by the transesterification of dioctyl terephthalate and butyl alcohol. However, since such esterification is performed at a higher temperature than the boiling point of a butyl alcohol reactant, there are issues that butyl alcohol can be vaporized during performing the reaction. In order to solve such problems, a large amount of butyl alcohol was used in the conventional process, and the vaporized butyl alcohol was cooled and condensed to be continuously refluxed in a reactor, but this method is still time consuming, requires a large amount of reactants and is costly.

PRIOR ART DOCUMENTS (Non-patent Document 1) Mustafizur Rahman and Christopher S. Brazel "The plasticizer market: an assessment of traditional plasticizers and research trends to meet new challenges" Progress in Polymer Science 2004, 29, 1223-1248

(Non-patent Document 2) N. R. Janjua et al. "Systemic Uptake of Diethyl Phthalate, Dibutyl Phthalate, and Butyl Paraben Following Whole-body Topical Application and Reproductive and Thyroid Hormone Levels in Humans" Environmental Science and Technology 2007, 41, 5564-5570

DISCLOSURE OF THE INVENTION

Technical Problem

An aspect of the present invention to solve the defects of the conventional art as described above is providing a method for manufacturing a terephthalate-based composition, which is more economic and decreases reaction time, by applying pressure in liquid injecting and reacting steps and preventing the vaporization of a primary alcohol reactant with a low boiling point and decreasing refluxing.

Technical Solution

According to an aspect of the present invention, there is provided a method for manufacturing a terephthalate-based composition, including a step of flowing in a dialkyl terephthalate in which alkyl has 7 to 10 carbon atoms and a primary alcohol with a low boiling point having 4 or 5 carbon atoms into a reactor, and performing transesterification of a terephthalate-based compound and the primary alcohol with a low boiling point (S1); and a step of extracting in a reduced pressure an unreacted material and a by-product from the reactor after finishing the transesterification (S2), wherein the step S1 includes a pressure-applying step in which the pressure of the reactor is set to 1.5 to 2.5 bar.

In the method for manufacturing a terephthalate-based composition of the present invention, the step S1 can further include a standard pressure step, the pressure-applying step can be 65% or more of a whole performing time period of the step S1, and the standard pressure step can be applied after the pressure-applying step in the step S1.

Advantageous Effects

In the manufacturing method of the present invention, the vaporization of a primary alcohol reactant with a low boiling point, is suppressed, and accordingly, a desired terephthalate-based composition can be manufactured even with a small amount of reactant in a short time, and energy consumption for refluxing, etc. can be reduced economically.

BRIEF DESCRIPTION OF THE DRAWINGS

The FIGURE is a simplified diagram of a process of an embodiment of the present invention.

MODE FOR CARRYING OUT THE INVENTION

Examples

Hereinafter, preferred embodiments will be suggested to assist the understanding of the present invention. The embodiments below are only for the illustration of the present invention and do not intend to limit the scope of the present invention.

In the Examples of the present invention, it was confirmed that if the composition ratio of the composition thus prepared fulfilled a reference after performing the reaction for a certain time in case where the step S1 included a pressure-applying step through simulation. The simulation was performed for a process for preparing a terephthalate-based composition including dioctyl terephthalate (DOT), butyloctyl terephthalate (BOTP) and dibutyl terephthalate (DBTP) using dioctyl terephthalate (DOTP) as a terephthalate-based compound, 1-butanol as a primary alcohol with a low boiling point, and TnBT as a catalyst, and the composition ratio of the butyloctyl terephthalate (BOTP) intermediate in the composition of 38.5±1% was set as a reference. The process was composed of liquid injecting, temperature elevating and reacting (70 minutes or 100 minutes), catalyst neutralizing and extracting steps, and in the catalyst neutralizing step, soda ash was used. A batch type reactor was selected as the reactor, and a simulation program used was Aspen Batch Modeler of AspenTech Co. A simplified diagram of the process of this embodiment is shown in The FIGURE.

Six Examples and two Comparative Examples in total were performed by changing the pressure and time of a pressure-applying step, the application or not of a standard pressure step and the time, and the pressure and time of the pressure-applying step, the application or not of the standard pressure step, and the time of each of the Examples and the Comparative Examples are summarized in Table 1 below.

TABLE 1

|  | Pressure-applying step | Standard pressure step | Total reaction time |
|---|---|---|---|
| Example 1 | 1.5 (70 min) | X | 70 min |
| Example 2 | 2.0 (70 min) | X | 70 min |
| Example 3 | 1.5 (50 min) | Standard pressure (20 min) | 70 min |
| Example 4 | 2.0 (50 min) | Standard pressure (20 min) | 70 min |
| Example 5 | 1.5 (45 min) | Standard pressure (25 min) | 70 min |
| Example 6 | 1.5 (55 min) | Standard pressure (15 min) | 70 min |
| Comparative Example 1 | X | Standard pressure (100 min) | 100 min |
| Comparative Example 2 | X | Standard pressure (70 min) | 70 min |

With respect to Examples 1 to 6, and Comparative Examples 1 and 2, the wt % of a reference material, a total refluxing amount, energy consumption, and an alcohol amount in an extract separated by extraction were calculated and are summarized in Table 2 below.

TABLE 2

|  | Reference material wt % | Total refluxing amount (kg) | Energy consumption (GJ) | Alcohol amount in extract (kg) |
|---|---|---|---|---|
| Example 1 | 100.2% | 5006 | 15.68 | 5504 |
| Example 2 | 100.2% | 2264 | 11.94 | 5495 |
| Example 3 | 100.0% | 6399 | 17.81 | 5481 |
| Example 4 | 100.4% | 6438 | 17.86 | 5549 |
| Example 5 | 100.0% | 6399 | 17.81 | 5481 |
| Example 6 | 100.0% | 6398 | 17.81 | 5482 |
| Comparative Example 1 | 100% | 8059 | 19.00 | 5480 |
| Comparative Example 2 | 99.8% | 17768 | 26.65 | 5479 |

In Comparative Example 2 in which the reaction was performed at standard pressure for 70 minutes, weak refluxing was generated at an initial liquid injecting step and strong refluxing was generated in a temperature elevating step, and the total refluxing amount was very large. However, in Examples 1 and 2 in which the reaction was performed for 70 minutes by applying a pressure in the whole step, the refluxing was weak in the liquid injecting and temperature elevating steps, and the total refluxing amount was significantly decreased. Particularly, the refluxing amount was largely decreased in Example 2 in which the pressure was applied to 2.0 bar. Meanwhile, in Examples 3 to 6 including a standard pressure step after applying a pressure, the total refluxing amount was larger than Examples 1 and 2 but was still significantly small when compared with Comparative Examples 1 and 2 in which the pressure was not applied at all. With this, it was confirmed that the pressure-applying step of the present invention restrained the refluxing and served assistance to the progress of the reaction.

The energy consumption is also proportional to the refluxing amount, and with the increase of the refluxing amount, the energy consumption increases. Accordingly, it was confirmed that comparative Examples 1 and 2 consumed the greatest amount of energy, but Examples 1 to 6 consumed a small amount of energy, and thus, the manufacturing method of the present invention was energy efficient.

With respect to the amount of alcohol in an extract separated by extraction, relating to extraction efficiency, Examples 1 to 6 showed greater amounts than Comparative Examples 1 and 2, and particularly, Example 4 showed the greatest amount. According to the manufacturing method of the present invention, it was confirmed that the amount of alcohol in an extract was large and showed better extraction efficiency than the method of the Comparative Examples.

Finally, it was confirmed that in Examples 1 to 6, the wt % of a reference material after finishing the reaction was 100% or more, and the reaction was sufficiently performed in a short reaction time of total 70 minutes, and an enough amount of a product was produced. On the contrary, in Comparative Example 2 in which the reaction was performed under the same conditions at a standard pressure for 70 minutes, the wt % of a reference material was 99.8%, and in Comparative Example 1 in which the reaction was performed for 30 minutes further, the wt % of a reference material was 100%. Accordingly, it was confirmed that if the manufacturing method of the present invention was used, the time used for the total process was largely reduced and a greater amount of a product or goods might be obtained in the same time period.

Hereinafter, the present invention will be described in more detail.

It will be understood that words or terms used in the specification and claims shall not be interpreted as the meaning defined in commonly used dictionaries. It will be further understood that the words or terms should be interpreted as having a meaning that is consistent with their meaning in the context of the relevant art and the technical idea of the invention, based on the principle that an inventor can properly define the meaning of the words or terms to best explain the invention.

The present invention provides a method for manufacturing a terephthalate-based composition including: a step of flowing in a dialkyl terephthalate in which alkyl has 7 to 10 carbon atoms and a primary alcohol with a low boiling point having 4 or 5 carbon atoms into a reactor, and performing transesterification of a terephthalate-based compound and the primary alcohol with a low boiling point (S1); and a step of extracting in a reduced pressure an unreacted material and a by-product from the reactor after finishing the transesterification (S2), wherein the step S1 includes a pressure-applying step in which the pressure of the reactor is set to 1.5 to 2.5 bar.

Hereinafter, the manufacturing method of the present invention will be explained step-by-step in detail.

Liquid Injecting and Reacting Steps (S1)

The manufacturing method of the present invention includes a step of flowing in a dialkyl terephthalate in which the alkyl has 7 to 10 carbon atoms and a primary alcohol with a low boiling point having 4 or 5 carbon atoms into a reactor, and performing transesterification of a terephthalate-based compound and the primary alcohol with a low boiling point (S1).

The step S1 is a step of injecting a dialkyl terephthalate and a primary alcohol with a low boiling point, which are reactants, to a reactor and reacting to obtain a terephthalate compound product which has undergone ester exchange.

The transesterification in the step S1 can be performed as the following Reaction 1:

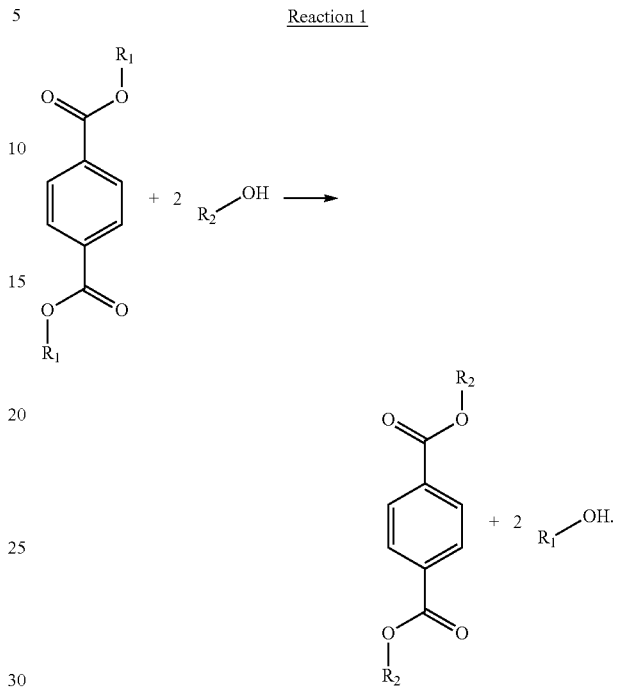

In Reaction 1, $C_6H_4(COOR_1)_2$ is a dialkyl terephthalate of which alkyl has 7 to 10 carbon atoms, and $R_2OH$ can be a primary alcohol with a low boiling point having 4 or 5 carbon atoms in $R_2$. The transesterification can be performed in the presence of an acid catalyst or a metal catalyst, and if a catalyst is used, a reaction time can decrease.

As the acid catalyst, sulfuric acid, methanesulfonic acid, p-toluenesulfonic acid or the like can be used, and as the metal catalyst, an organometal catalyst, a metal oxide catalyst, a metal salt catalyst or the metal itself can be used. As the metal component of the metal catalyst, tin, titanium, zirconium or the like can be used, and titanium is preferably used. The catalyst used in the transesterification can particularly be tetra-n-butyl titanate (TnBT) or methanesulfonic acid, and most preferably, TnBT is used.

The catalyst can be a catalyst which requires a neutralizing step of the catalyst later.

The neutralizing step of the catalyst can be performed after the step S1 and prior to the extracting step S2.

The catalyst neutralization can be performed using an aqueous solution of soda ash or caustic soda and can preferably be performed using soda ash.

As the product of the transesterification, a dialkyl terephthalate of which alkyl has 4 or 5 carbon atoms is produced, and an alcohol of 7 to 10 carbon atoms is produced as a by-product. The by-product can become a target for distillation in a reduced pressure together with an unreacted material later.

The dialkyl terephthalate reactant of which alkyl has 7 to 10 carbon atoms is preferably di(2-ethylhexyl) terephthalate, and the primary alcohol with a low boiling point having 4 or 5 carbon atoms is preferably butanol.

The transesterification can be performed at a temperature of 130 to 185° C., preferably, 135 to 180° C., more preferably, 140 to 170° C. Accordingly, the step S1 can include a temperature elevating step for elevating the temperature of the reactor after injecting a liquid. If the temperature of the reactor is lower than 130° C., energy required for the reaction is insufficiently supplied, and the reaction may not proceed smoothly. If the temperature is higher than 185° C., the alcohol produced as the by-product vaporizes together with the unreacted material, and the refluxing of a portion of the vaporized reactant can become difficult.

In the conventional method for manufacturing a terephthalate-based composition, the boiling point of the primary alcohol reactant with a low boiling point is lower than the temperature required for the transesterification, and there are defects of vaporizing the primary alcohol in the liquid injecting and temperature elevating steps. If the primary alcohol with a low boiling point is vaporized, the concentration of the reactant decreases, and since the above-described esterification is an equilibrium reaction, if the concentration of the reactant decreases, chemical equilibrium shifts toward reactants and time to reach equilibrium increases. Accordingly, such defects have been solved by using an excessive amount of the primary alcohol reactant with a low boiling point and condensing and refluxing the vaporized primary alcohol with a low boiling point again. However, such a solution method also has another defect that energy used for refluxing is large and a reaction time is increased, because a process of flowing in the reactant to the reactor back through refluxing is continuously performed during the reaction.

Meanwhile, in the transesterification, the primary alcohol with a low boiling point has a lower boiling point than the reaction temperature, the amount vaporized in the temperature elevating step of the reactor after injecting a liquid can be the largest, and accordingly, the amount refluxed can also become the largest. In addition, the liquid injecting, temperature elevating and reacting steps are not substantially clearly distinguished, but toward the latter period of the reaction, the concentration of the reactant decreases due to the progress of the reaction, and thus, the amount vaporized can decrease. However, the vaporization is generated continuously, and accordingly, in order to achieve a desired component ratio and yield of the terephthalate-based composition as a product, the amount vaporized of the primary alcohol with a low boiling point is required to be controlled through the whole reaction.

Therefore, the inventors of the present invention try to suggest a method for manufacturing a terephthalate-based composition, by which reaction time delay problem or energy problem due to refluxing can be solved and the productivity of the whole reaction can be improved, through limiting the vaporization of the primary alcohol with a low boiling point by appropriately increasing the pressure of the reactor in the liquid injecting, temperature elevating and reacting steps.

Particularly, the step S1 in the method for manufacturing a terephthalate-based composition of the present invention includes a pressure-applying step so that the pressure of the reactor becomes 1.5 to 2.5 bar, and preferably, can include a pressure-applying step so that the pressure of the reactor becomes 1.5 to 2.0 bar. If the pressure in the step S1 is lower than 1.5 bar, there are problems that the vaporization of the primary alcohol with a low boiling point among the reactants can be insufficiently prevented, and if the pressure is higher than 2.5 bar, there are problems of increasing energy required in an extracting step which is to be performed in a reduced pressure and inducing the decrease of extraction efficiency, and in addition, there are problems of excessively increasing the installation expenses of the entire process, because the designs of a reactor, a heat exchanger, etc., which are used in the reaction are required to be changed so that the corresponding equipment can endure a high pressure of greater than 2.5 bar for smooth performance of the reaction. The pressure-applying step in the step S1 can be the whole of the step S1. Since the primary alcohol with a low boiling point can produce a large refluxing amount during liquid injecting and temperature elevating and vaporization is continuously happened, in order to prevent the vaporization of the primary alcohol with a low boiling point to the utmost limit, the reaction can be performed while applying a pressure in the whole of the step S1.

More preferably, the step S1 can further include a standard pressure step in addition to the pressure-applying step, and the pressure-applying step can occur during 65% or more of the whole time period of the step S1. More preferably, the pressure-applying step can be from 65% to 80% of the whole performing time period of the step S1, and the standard pressure step can be additionally applied besides the specified pressure-applying step.

If the step S1 includes the standard pressure step and the length of the pressure-applying step is less than 65% of the whole performing time period, the technical advantages of the present invention due to the pressurizing, that is, effects of preventing the vaporization of the primary alcohol with a low boiling point among the reactants can be insufficiently achieved. In addition, if the length of the pressure-applying step is greater than 80% of the performing time of the whole step S1, the amount of alcohol in the reaction product can increase after the step S2, and the alcohol can act as impurities in a subsequent process.

If the step S1 includes the standard pressure step, in view of connectivity with a subsequent extracting step (S2), the standard pressure step is preferably applied after the pressure-applying step. This is because in the extracting step (S2) which is performed in a reduced pressure after the step S1, the pressure decrease in a relatively lower pressure in the standard pressure step is more efficient than in the high pressure of the pressure-applying step. In addition, if the pressure-applying step is applied after the standard pressure step and the standard pressure step is not recovered later, there are additional problems that the amount of by-products in waste water which is generated after neutralization in a catalyst neutralizing step which can be performed prior to the extracting step (S2), can increase to increase the treatment cost of the waste water.

Further, for the purpose of preventing the vaporization of the primary alcohol with a low boiling point, the whole step can preferably be a pressure-applying step, but in view of smooth connection with a subsequent extracting step and the productivity of the whole reaction, it can be preferable that the pressure-applying step can be a part of the whole step S1 as described above.

As the reactor used in the manufacturing method of the present invention, anything can be used without limitation as far as it is commonly used in transesterification. For example, a batch type reactor can be used.

Extracting Step (S2)

The manufacturing method of the present invention includes after finishing the reaction, an extracting step (S2) in a reduced pressure of an unreacted material and a by-product from the reactor.

In the manufacturing method of the present invention, the unreacted material and the by-product can be extracted in a reduced pressure from the reactor after finishing the reaction, and a terephthalate-based composition remaining in the reactor can be obtained in a desired composition ratio. By decreasing the pressure of the reactor including the unreacted material and the by-product, the unreacted material and the by-product can be efficiently extracted from the top of the reactor, and by appropriately controlling a vacuum pressure during reducing the pressure, the terephthalate-based composition can be obtained in a high purity.

In the step S2, the unreacted material is a primary alcohol with a low boiling point of 4 or 5 carbon atoms, and the by-product is a primary alcohol with a high boiling point of 7 to 10 carbon atoms, which is produced by the transesterification.

The unreacted material extracted and separated in the step S2 can be reused in a next preparation process.

The extraction in a reduced pressure can be performed using various equipment and methods as long as the physical properties of the terephthalate-based composition thus prepared are not damaged, and a person skilled in the art can select appropriate equipment and method for decreasing a pressure and extracting considering the whole process to perform the present invention.

The invention claimed is:

1. A method for manufacturing a terephthalate-based composition, the method comprising:
   step (S1) of flowing in a dialkyl terephthalate in which alkyl has 7 to 10 carbon atoms and a primary alcohol with a low boiling point having 4 or 5 carbon atoms into a reactor and performing transesterification of the dialkyl terephthalate and the primary alcohol with a low boiling point; and
   a step (S2) of extracting in a reduced pressure an unreacted material and a by-product from the reactor after finishing the transesterification,
   wherein the step S1 comprises a pressure-applying step in which the pressure of the reactor is 1.5 to 2.5 bar, and a standard pressure step in which the pressure of the reactor is standard pressure, and
   wherein the pressure-applying step occurs during 65% or more of a whole time period of the step S1.

2. The method according to claim 1, wherein the pressure-applying step occurs during 65% to 80% of a whole time period of the step S1.

3. The method according to claim 1, wherein the standard pressure step is applied after the pressure-applying step in step S1.

4. The method according to claim 1, wherein in the pressure-applying step the pressure of the reactor is 1.5 to 2.0 bar.

5. The method according to claim 1, wherein the dialkyl terephthalate is di(2-ethylhexyl) terephthalate.

6. The method according to claim 1, wherein the primary alcohol with a low boiling point is butanol.

7. The method according to claim 1, wherein the unreacted material is a primary alcohol with a low boiling point having 4 or 5 carbon atoms, and the by-product is a primary alcohol with a high boiling point having 7 to 10 carbon atoms, which is produced by the transesterification.

8. The method according to claim 1, wherein the reactor is a batch type reactor.

* * * * *